United States Patent [19]
Say

[11] Patent Number: 6,128,519
[45] Date of Patent: Oct. 3, 2000

[54] SYSTEM AND METHOD FOR MEASURING A BIOANALYTE SUCH AS LACTATE

[75] Inventor: James I Say, Alameda, Calif.

[73] Assignee: Pepex Biomedical, LLC, Villa Park, Calif.

[21] Appl. No.: 09/212,557

[22] Filed: Dec. 16, 1998

[51] Int. Cl.[7] .................................................. A61B 5/05
[52] U.S. Cl. ............................................ 600/345; 600/309
[58] Field of Search .................................... 600/345, 366, 600/368, 322, 309, 347

[56] References Cited

U.S. PATENT DOCUMENTS

| | | | |
|---|---|---|---|
| 4,240,438 | 12/1980 | Updike et al. | 600/347 |
| 4,786,394 | 11/1988 | Enzer et al. | 204/401 |
| 4,830,011 | 5/1989 | Lim | 600/345 |
| 5,330,634 | 7/1994 | Wong et al. | 205/777.5 |
| 5,505,828 | 4/1996 | Wong et al. | |
| 5,697,366 | 12/1997 | Kimball et al. | 600/309 |
| 5,976,085 | 11/1999 | Kimball et al. | 600/309 |
| 6,027,445 | 2/2000 | Von Bahr | 600/309 |

FOREIGN PATENT DOCUMENTS

| | | |
|---|---|---|
| WO 94/21163 | 9/1994 | WIPO . |
| WO 98/32013 | 7/1998 | WIPO . |

*Primary Examiner*—Cary O'Connor
*Assistant Examiner*—Navin Natnithithadha
*Attorney, Agent, or Firm*—Merchant & Gould P.C.

[57] ABSTRACT

The present disclosure relates to a sensor assembly including a catheter having a catheter sheath adapted for insertion in a patient, and a catheter hub connected to the catheter sheath. An adapter is connected to the catheter hub. The adapter includes first and second ports. A first flow line extends between the first port and a pump. A sensor is positioned along the first flow line. A second flow line extends between the second port and a container for holding a calibration fluid. The adapter defines first and second separate passages. The first passage extends from the first port to an interior region of the catheter sheath. The second passage extends from the second port to the interior region of the catheter hub.

25 Claims, 10 Drawing Sheets

SYSTEM AND METHOD FOR MEASURING A BIOANALYTE SUCH AS LACTATE

FIELD OF THE INVENTION

This invention relates generally to systems and methods for measuring bioanalytes. More particularly, the present invention relates to systems and methods for measuring lactate.

BACKGROUND OF THE INVENTION

For critical care patients, physicians have long relied on personal examination and clinical laboratory results to determine the presence and concentration of biological analytes in a patient. Clinical laboratories offer a wide range of automated systems for high-volume testing and analytical support in a well controlled, high quality environment. However, clinical laboratories can not provide the immediate results needed to properly treat trauma and multi organ dysfunction/failure patients.

To meet the clinical need for immediate test results, several technologies are emerging for testing using reliable, automated analyzers at the patient's bedside. This type of testing is commonly termed point-of-care (POC) diagnostic testing. POC diagnostic test systems include electrochemical biosensors, optical fluorescence sensors, paramagnetic particles for coagulation test systems, and micromachined devices for both chemical and immunochemical testing. These technologies have allowed multi-analyte chemistry panels to be performed rapidly and have addressed previous obstacles such as calibration of test devices. POC tests can be classified as: 1) in vitro, which is performed at the bedside; 2) ex vivo or para vivo, which is performed at wrist-side; and 3) in vivo, which is performed inside the patient. POC tests offer indirect cost efficiencies and savings such as reduced labor costs, decreased blood identification and transport errors, and reduced patient complications.

In vitro or bedside POC devices are used typically in several departments of the hospital including intensive care units; operating rooms; emergency departments (ER); interventional departments; general patient care departments; and outpatient surgery and ambulatory care units. In vitro POC diagnostic tests offer a wide range of diagnostic tests, similar to the clinical laboratory. In vitro POC diagnostic test systems typically are not connected on-line to the patient and require an operator for blood sampling. Key categories of diagnostic test in the POC diagnostic market include arterial blood gases, blood chemistries, blood glucose, coagulation, drugs-of-abuse testing, hemoglobin, hematocrit, infectious diseases, and therapeutic drug monitoring. Other categories include cancer markers, cardiac markers, cholesterol detection, immunodiagnostics, infectious disease detection, lactate, and thrombolytic monitoring.

Ex vivo POC diagnostics use external sensors for on-line real-time testing with little to no blood loss. Typically, sampled blood flows through a closed system to minimize blood contact. Ex vivo POC systems minimize problems associated with in vivo sensors, including clotting, inaccuracy, calibration drift, and an inability to recalibrate once in the patient. Optical Sensors, Inc. of Minneapolis, Minnesota currently markets ex vivo blood gas analyzers which utilize a hand operated syringe system. VIA Medical Corporation of San Diego, California markets ex vivo blood glucose analyzers which utilize a relatively large volume, automated sampling and analysis system. U.S. Pat. No. 5,505,828 discloses an exemplary ex vivo POC system.

In vivo POC diagnostics offer considerable potential in the treatment of most critical and unstable patients. Although many companies are developing in vivo sensors, technical hurdles have thus far kept in vivo sensors from common commercial use.

Ex vivo and in vivo POC diagnostics, since they are on-line systems, can reduce quality control and information integration errors that occur with clinical or in vitro POC tests. Quality control errors are commonly due to operator errors, not instrument errors or device failures. Exemplary errors include inappropriate specimen volume, inaccurate calibration, use of deteriorated test strips, inadequate validation, insufficient instrument maintenance, bad timing of the test procedure, and use of the wrong materials. Clinical information system integration allows test data collected at the bedside to be put directly into the patient record. This improves the efficiency of the patient management process, allowing the integration of the laboratory's information system and clinical information systems, providing a "seamless" flow of all types of patient information.

SUMMARY OF THE INVENTION

One aspect of the present invention relates to a sensor assembly including a catheter having a catheter sheath adapted for insertion in a patient, and a catheter hub connected to the catheter sheath. An adapter is connected to the catheter hub. The adapter includes first and second ports. A first flow line extends between the first port of the adapter and a pump. A sensor is positioned along the first flow line. A second flow line extends from the second port of the adapter to a container for holding a calibration fluid. The calibration fluid includes a calibrant adapted for use in calibrating the sensor. The adapter of the sensor assembly defines first and second separate passages. The first passage extends from the first port to an interior region of the catheter sheath. The second passage extends from the second port to an interior region of the catheter hub.

Another aspect of the present invention relates to a sensor assembly including a catheter having a catheter sheath adapted for insertion in a patient. The assembly also includes a first structure defining a first flow passage that terminates within an interior region of the catheter sheath, and a second structure defining a second flow passage separate from the first flow passage that also terminates within the interior region of the catheter sheath. A sensor is positioned in fluid communication with the first flow passage, and a source of calibration fluid is in fluid communication with the second flow passage. The assembly further includes a pump in fluid communication with the first flow passage.

A further aspect of the present invention relates to a method of operating a sensor assembly as described above. The method includes inserting the catheter sheath into the patient. The method also includes conveying calibration fluid through the second flow passage from the source of calibration fluid into the interior region of the catheter sheath. The method further includes calibrating the sensor by pumping the calibration fluid from the interior region of the catheter sheath through the first flow passage, and conveying the calibration fluid past the sensor. After the sensor has been calibrated, a sample fluid is drawn from the patient by terminating the conveyance of calibration fluid to the interior region of the catheter sheath, and pumping a sample fluid from the interior region of the catheter sheath through the first flow line to the sensor. Finally, the sample fluid is sensed by the sensor.

Still another aspect of the present invention relates to an adapter for use with a catheter including a catheter sheath connected to a catheter hub. The catheter sheath is adapted for insertion in a patient. The adapter includes an adapter body defining first and second ports adapted for connection to medical tubing. The adapter also includes a connecting member adapted to fasten the adapter body to the hub. The adapter further includes a conduit extending from the first port through the adapter body. The conduit includes an end portion that projects outward from the adapter body. The end portion is arranged and configured to fit within an interior region of the catheter sheath when the adapter body is connected to the catheter hub. The adapter additionally includes structure defining a passage separate from the conduit that extends from the second port through the adapter body to the catheter sheath.

These and various other features which characterize the invention are pointed out with particularity in the attached claims. For a better understanding of the invention, it's advantages, and objectives obtained by its use, reference should be made to the drawings and to the accompanying description, in which there is illustrated and described preferred aspects of the present invention.

BRIEF DESCRIPTION OF THE DRAWINGS

The accompanying drawings, which are incorporated in and constitute a part of this specification, illustrate several aspects of the invention and together with the description, serve to explain the principles of the invention. A brief description of the drawings is as follows:

FIG. 2 is an exploded view of an adapter suitable for use with the sensor assembly of FIG. 1;

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

An aspect of the present invention relates to systems and methods for providing on-line monitoring/measurement of bioanalytes in a patient. One particular aspect of the present invention relates to systems and methods for providing on-line measurement of lactate concentrations in a patient.

Lactate is a small molecule that is produced by all tissues and organs of a patient's body that are in "distress". Wherever in the patient's body the demands for oxygen exceed the supply, then a state of low perfusion exists and lactate is produced. For example, lactate is produced if a patient is bleeding, if a patient's heart is failing, if a person's limb is in danger of being lost, or if a person is not getting enough oxygen to breathe. Thus many life and limb threatening clinical states produce elevated blood lactate levels, even in the face of adequate oxygen delivery to the patient. It is a matter of oxygen supply and metabolic demand.

At the cellular level, lactate is inversely proportional to the vital cellular energy stores of adenosine triphosphate and is produced within six seconds of inadequate perfusion or cellular injury. It is thus an ideal biochemical monitor of cellular viability at the tissue level, and of patient viability at the systemic level.

Clinically, the dire significance of elevated and rising blood lactate values is known. Trauma physicians and clinical evidence support the hypothesis that a simple, inexpensive, continuous, monitor of lactate in the trauma setting, will save lives by providing timely, life-saving information that will help dictate triage and therapy. For example, an emergency room patient who has a blood lactate level of 4 mM has a 92% mortality rate within the next 24 hours. If this level is 6 mM, then the mortality rate rises to 98%. In animal experiments, blood lactate levels begin to rise within minutes of hemorrhage, and conversely, begin to fall just as quickly with adequate resuscitation. In multivariate analysis, blood lactate is the best indicator of the degree of shock (superior to blood pressure, heart rate, urine output, base deficit, blood gas and Swan-Ganz data) and is proportional to the shed blood volume. Blood lactate levels correlate with a trauma patient's chances of survival. Therapy that fails to control a patient's increasing lactate levels must be modified or additional diagnoses quickly sought.

Figure 1:
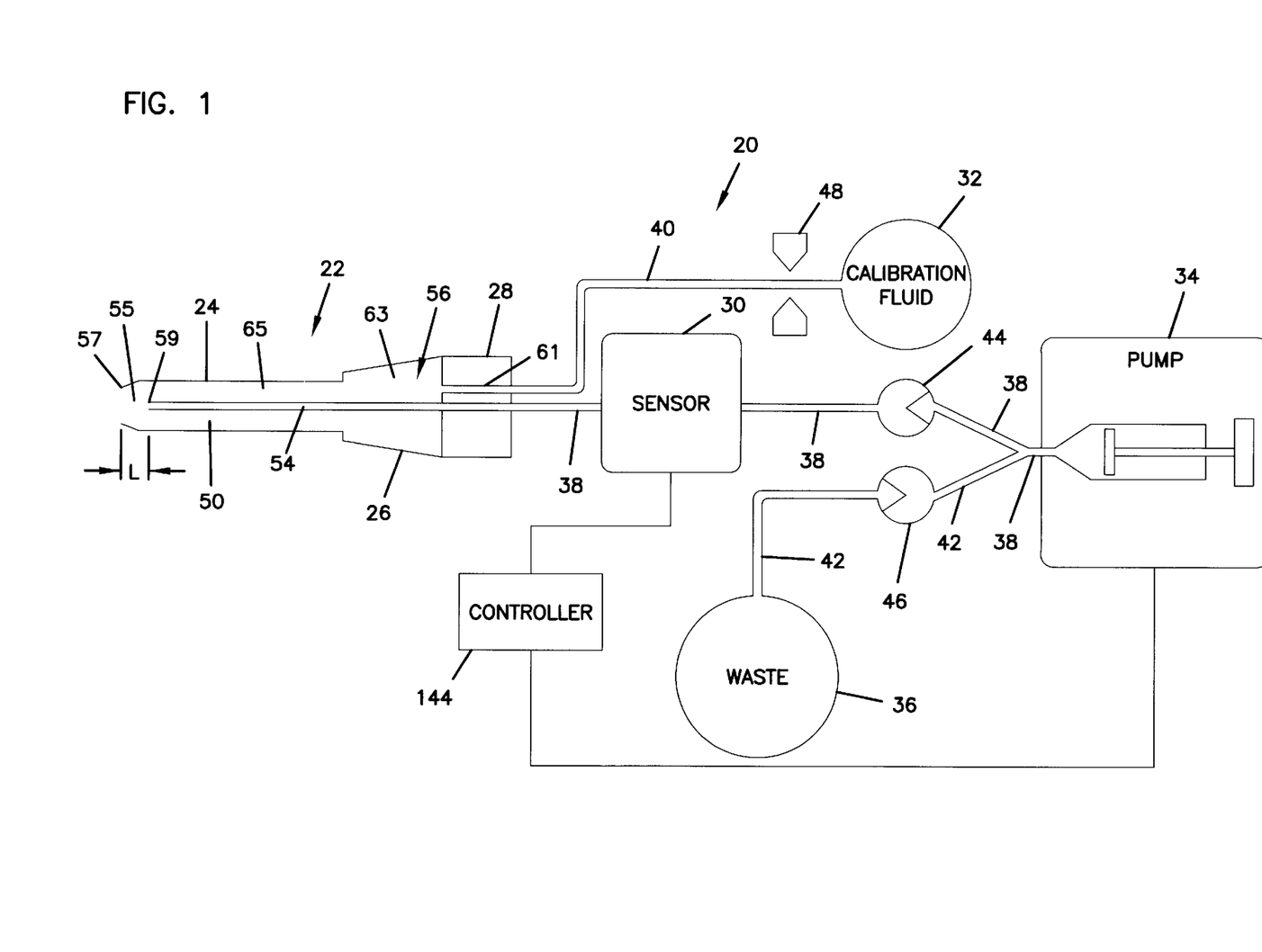
FIG. 1 is a schematic illustration of an embodiment of a sensor assembly constructed in accordance with the principles of the present invention.

FIG. 1 schematically shows a sensor assembly 20 for providing on-line monitoring/measurement of bioanalytes such as lactate in a patient. The sensor assembly 20 includes a catheter 22 (e.g., a peripheral catheter) including a catheter sheath 24 connected to a catheter hub 26 (i.e., a luer fitting). The sensor assembly 20 also includes an adapter 28 connected to the catheter hub 26, a sensor 30, a source of calibration fluid 32, a pump 34 (e.g., a syringe driven by a syringe driver) and a waste container 36 (e.g., a waste bag). A first flow line 38 connects the adapter 28 to the pump 34. The sensor 30 is positioned along the first flow line 38. A second flow line 40 interconnects the adapter 28 and the source of calibration fluid 32. A third flow line 42 extends between the first flow line 38 and the waste container 36. A controller 144 (e.g., a micro-controller, a mechanical controller, a software driven controller, a hardware driven controller, a firmware driven controller, etc.) preferably interfaces with both the sensor 30 and the pump 34.

The first flow line 38 provides fluid communication between the adapter 28 and the pump 34. The first flow line 38 functions to convey fluid from the adapter 28 through the sensor 30. A first check valve 44 is positioned along the first flow line 38 at a location between the sensor 30 and the pump 34. The first check valve 44 allows fluid to flow through the first flow line 38 in a direction from the adapter 28 toward the pump 34, but prevents or blocks fluid flow through the first flow line 38 in a direction from the pump 34 toward the adapter 28. The third flow line 42 branches off from the first flow line 38 at a location positioned between the first check valve 44 and the pump 34. A second check valve 46 is positioned along the third flow line 42. The second check valve 46 allows fluid flow through the third flow line 42 in a direction toward the waste container 36, but blocks or prevents fluid flow through the third flow line 42 in a direction away from the waste container 36.

The second flow line 40 functions to convey calibration fluid from the source of calibration fluid 32 to the adapter 28. A valve structure such as a pinch valve 48 is used to selectively open and close the second flow line 40. When the second flow line 40 is open, calibration fluid flows through the second flow line 40 to the adapter 28. When the second flow line 40 is closed, the flow of calibration fluid to the adapter 28 is stopped.

The adapter 28 and the catheter 22 of the sensor assembly 20 preferably cooperate to provide two separate passages that respectively connect the first and second flow lines 38 and 40 to a fluid exchange region 55. Preferably the fluid exchange region 55 is located within an interior region 50 of the catheter sheath 34 adjacent to a distal tip 57 of the catheter sheath 24. As shown in FIG. 1, the adapter 28 defines a first passage 54 that extends from the first flow line 38, through the catheter hub 26, to the interior region 50 of the catheter sheath 24. The first passage 54 terminates within the interior volume 50 of the sheath 24 at the fluid exchange region 55. The first passage 54 has a termination location 59 (i.e., the location of the tip of the conduit defining the first passage 54) that is spaced a length L from the distal tip 57 of the catheter sheath 24. In one particular embodiment, the length L does not exceed 1 centimeter. In another particular embodiment, the length L does not exceed 5 millimeters. In a further embodiment, the length L does not exceed 2 millimeters. In still another embodiment, the length L does not exceed 1 millimeter.

Referring again to FIG. 1, the adapter 28 and the catheter 22 cooperate to define a second passage 56 that extends from the second flow line 40 to the fluid exchange region 55. The second passage 56 includes a first portion 61 defined through the adapter 28, a second portion 63 defined through the catheter hub 26, and a third portion 65 defined through the catheter sheath 24. The portions 61, 63 and 65 are all in fluid communication with one another. For example, the first portion 61 extends through the adapter 28 from the second flow line 40 to the second portion 63, the second portion extends through the catheter hub 26 from the first portion 61 to the third portion 65, and the third portion 65 extends through the catheter sheath 24 from the second portion 63 to the fluid exchange region 55. Preferably, the second and third portions 63 and 65 of the second passage 56 concentrically surround the first passage 54.

FIG. 2 provides an exploded illustration of the various components of an adapter 28' suitable for use with the sensor assembly 20. Generally, the adapter 28' includes an insertion portion 58, a connecting member or collar 60, a fluid manifold 62, a dual tube receiver 64, a draw tube or conduit 66 and a tubing step-down connector 68 connected to the conduit 66.

The insertion portion 58 of the adapter 28' is generally cylindrical and includes a first end 70 positioned opposite from a second end 72. A radial shoulder 74 projects outward from the insertion portion 58 at a location intermediate the first and second ends 70 and 72. Adjacent the first end 70, the insertion portion 58 includes a frustral conical shaped portion 76. The frustral conical shaped portion has a minor diameter located directly at the first end 70 of the insertion portion 58, and a major diameter located adjacent to the radial shoulder 74. The frustral conical shaped portion 76 has an exterior taper that compliments a corresponding taper 77 of an interior region 77 of the catheter hub 26 such that the frustral conical shaped portion 76 is sized and shaped to be received within the catheter hub 26.

The insertion portion 58 defines an axial bore 78 that extends completely through the insertion portion 58 between the first and second ends 70 and 72. The axial bore 78 has an enlarged diameter portion 79 positioned adjacent the second end 72 of the insertion portion 58, and a reduced diameter portion 80 that extends through the first end 70 of the insertion portion 58. A tapered transition region 82 is defined between the enlarged diameter portion 79 and the reduced diameter portion 80.

The collar 60 of the adapter 28' is preferably generally cylindrical and defines a generally cylindrical inner chamber 84 sized to receive the catheter hub 26. The collar 60 preferably defines a plurality of interior threads positioned within the inner chamber 84. The interior threads are preferably configured such that the collar 60 can be threaded on corresponding exterior threads formed on the outer surface of the catheter hub 26. The collar 60 also includes a radial end wall 86 defining a central opening 88 sized for receiving the second end 72 of the insertion portion 58.

The fluid manifold 62 of the adapter 28' includes a main portion 90 and an extension 92 that projects axially outward from the main portion 90. The extension 92 is generally cylindrical and includes an inner axial opening 94 sized for receiving the second end 72 of the insertion portion 58. At an end opposite the extension portion 92, the main portion 90 defines a recess 96. The main body 90 also includes a circumferential shoulder 98 that projects radially into the recess 96.

The dual tube receiver 64 of the adapter 28' defines first and second ports 100 and 102. The first port 100 is sized for receiving the step-down connector 68 connected to the conduit 66. In turn, the step down connector 68 is sized to receive an end of the first flow line 38. The second port 102 is sized to receive an end of the second flow line 40. The dual tube receiver 64 includes a reduced diameter portion 104 sized to fit within the recess 96 of the fluid manifold 62.

Figure 3:
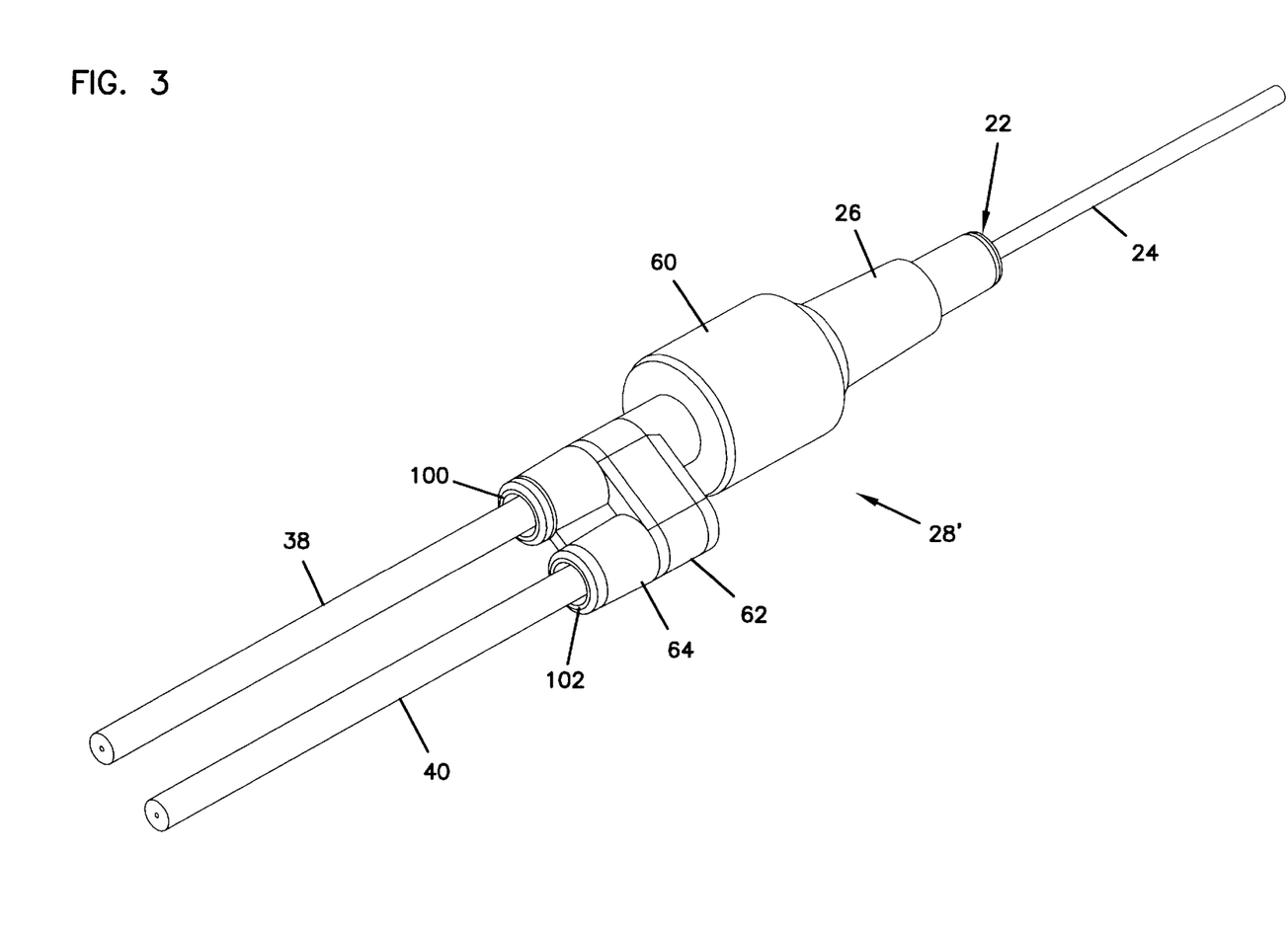
FIG. 3 is an assembled perspective view of the adapter of FIG. 2.
Figure 4:
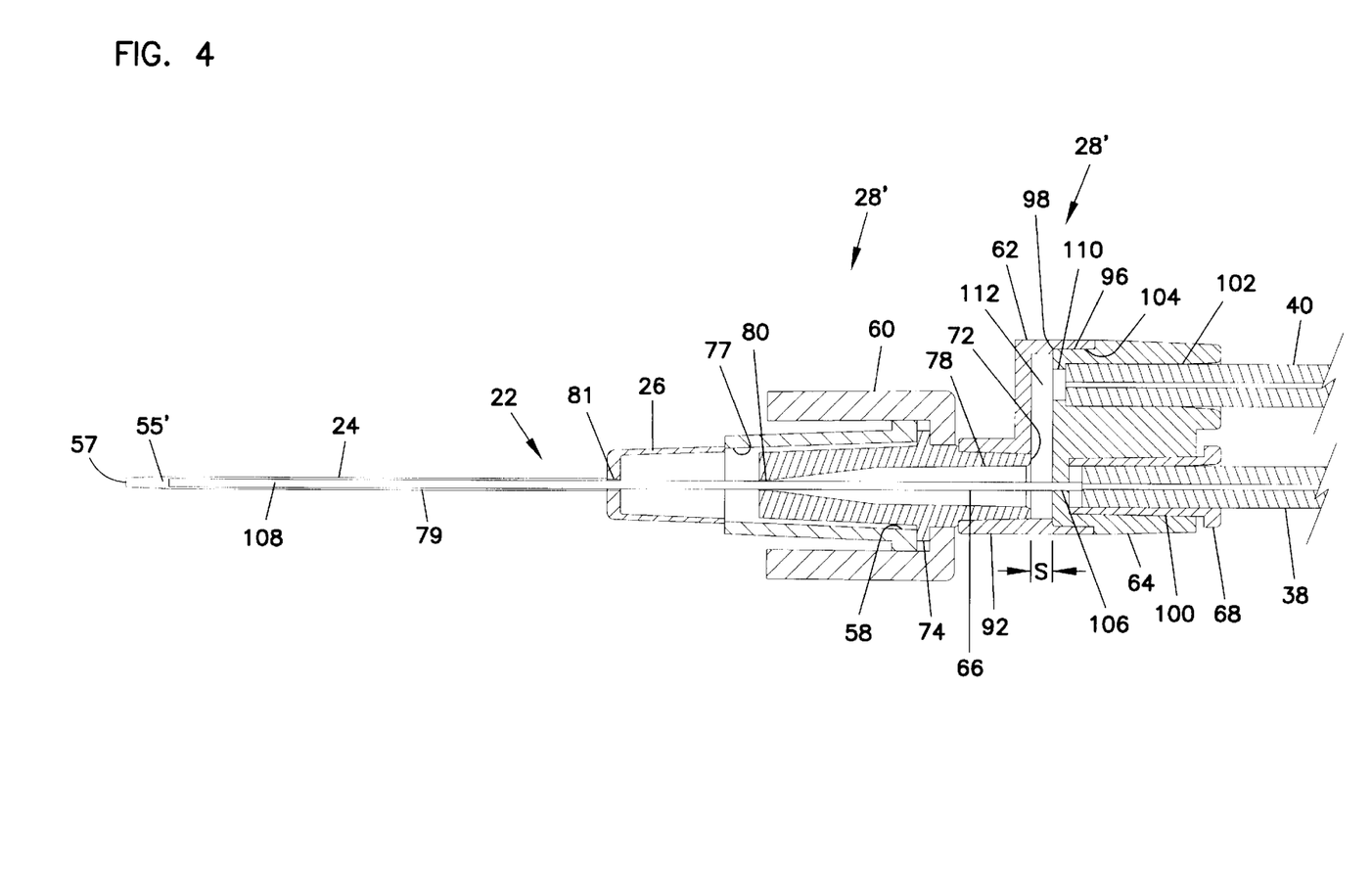
FIG. 4 is a cross-sectional view cut lengthwise through the adapter of FIG. 3.

FIGS. 3 and 4 show the adapter 28' as assembled. As shown best in FIG. 3, the second end 72 of the insertion portion 58 is inserted within the extension 92 of the fluid manifold 62. Also, the reduced diameter portion 104 of the dual tube receiver 64 is inserted within the recess 96 of the fluid manifold 62. The insertion portion 58, the fluid manifold 62 and the dual tube receiver 64 are preferably bonded together to form a main adapter body.

Referring to FIG. 4, the collar 60 is rotatably mounted between the radial shoulder 74 of the insertion portion 58 and the extension 92 of the fluid manifold 62. Also, the step-down connector 68 is mounted within the first port 100 of the dual tube receiver 64, and the first flow line 38 is press fit within the step-down connector 68. Similarly, the second flow line 40 is press fit within the second port 102.

Still referring to FIG. 4, the conduit 66 extends axially from the step down connector 68 through an opening 106 defined by the dual tube receiver 64 into the insertion portion 58. Within the insertion portion 58, the conduit 66 extends axially through the axial bore 78. An end portion 108 of the conduit projects axially outward from the first end 70 of the insertion portion 58.

To exit the insertion portion 58, the conduit 66 extends through the reduced diameter portion 80 of the insertion portion 58. In one particular embodiment, the reduced diameter portion 80 has a diameter of 0.030 inch, and the conduit 66 has an outer diameter of 0.016 inch. Such a variation in diameters provides a relatively loose fit between the conduit 66 and the reduced diameter portion 80. The relatively loose fit between the conduit 66 and the reduced diameter portion 80 allows fluid traveling through the axial bore 78 to exit the insertion portion 58 through the reduced diameter portion 80. Fluid exiting the axial bore 78 circumferentially/concentrically surrounds the conduit 66 as it travels through the reduced diameter portion 80.

Referring still to FIG. 4, the adapter 28' defines a flow passage that extends from the second flow line 40 axially through an opening 110 defined by the dual tube receiver 64. The passage then extends along a radial passage portion 112 defined between the fluid manifold 62 and the dual tube receiver 64. The reduced diameter portion 104 of the dual tube receiver 64 abuts against the circumferential shoulder 98 of the fluid manifold 62 such that an axial spacing S of the radial passage portion 112 is maintained. From the radial passage portion 112, the passage extends in an axial direction along the axial bore 78 of the insertion portion 58.

When the adapter 28 is connected to the catheter hub 26, the insertion portion 58 fits within the catheter hub 26 and the collar 60 is threaded on the exterior of the catheter hub 26. In such a configuration, the first end 70 of the insertion portion 58 projects into the interior cavity 77 of the catheter hub 26, and the end portion 108 of the conduit 66 projects or extends into the interior of the catheter sheath 24. The tip of the conduit 66 is preferably positioned at a fluid exchange region 55' located adjacent the distal tip 57 of the catheter sheath 24. Fluid communication is provided between the axial bore 78 of the adapter 28 and the interior cavity 77 of the catheter hub 26 via the reduced diameter portion 80 of the axial bore 78 (i.e., fluid in the axial bore 78 can enter the catheter hub 26 by flowing between the conduit 66 and the region of the insertion portion 58 that defines the reduced diameter portion 80.) Fluid communication is also provided between the interior cavity 77 of the hub 26 and the interior of the catheter sheath 24. For example, the hub defines an end opening 81 that is sufficiently larger than the conduit 66 to allow fluid to freely flow between the interior cavity 77 of the hub 26 and an annular passage 79 that surrounds the conduit 66 within the sheath 24. The annular passage 79 is defined between the conduit 66 and the catheter sheath 24 and is configured to convey fluid from the interior cavity 77 of the hub 26 to the fluid exchange region 55'.

Figure 5:
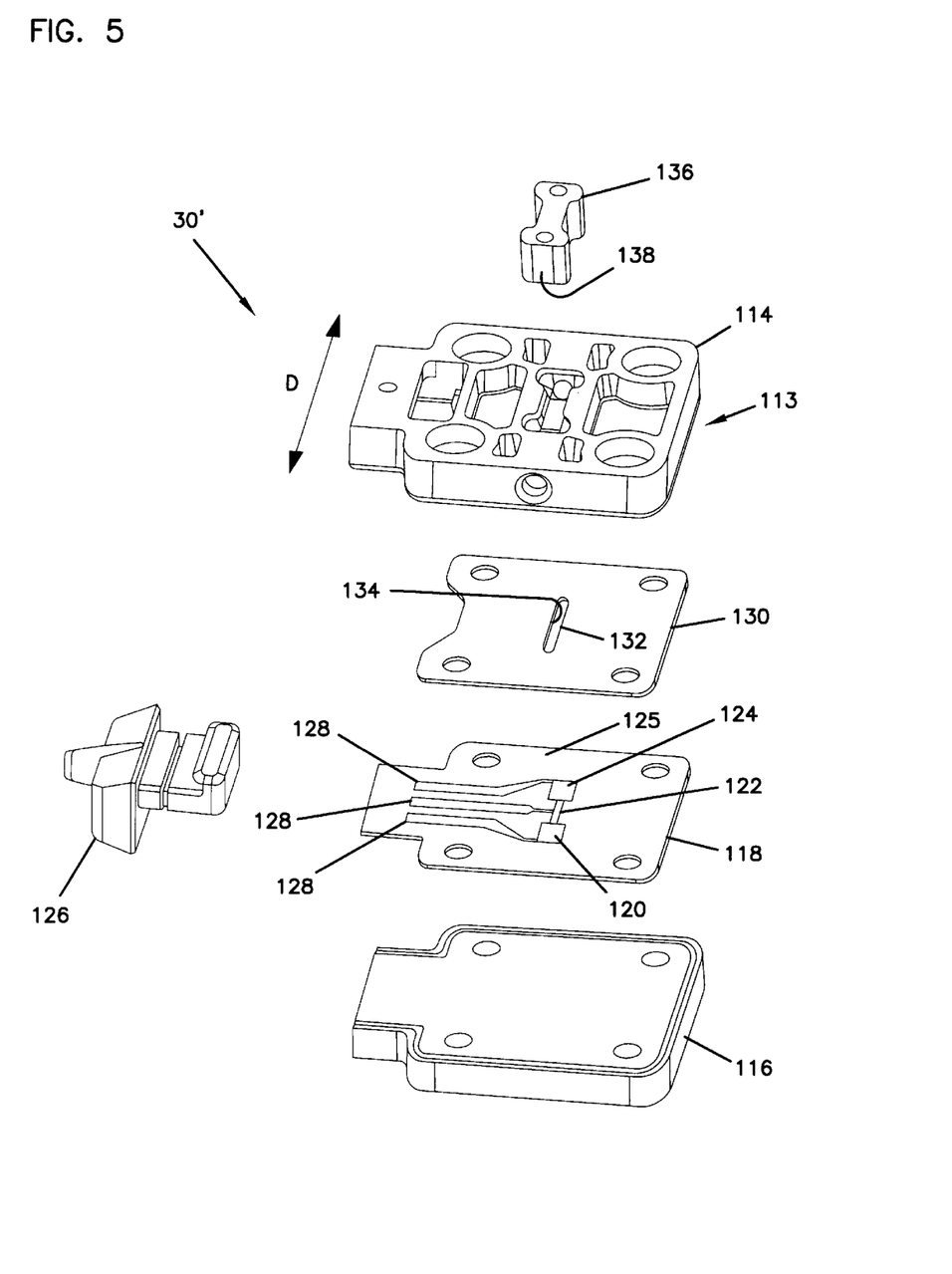
FIG. 5 is a exploded view of a sensor module suitable for use with the sensor assembly of FIG. 1.
Figure 6:
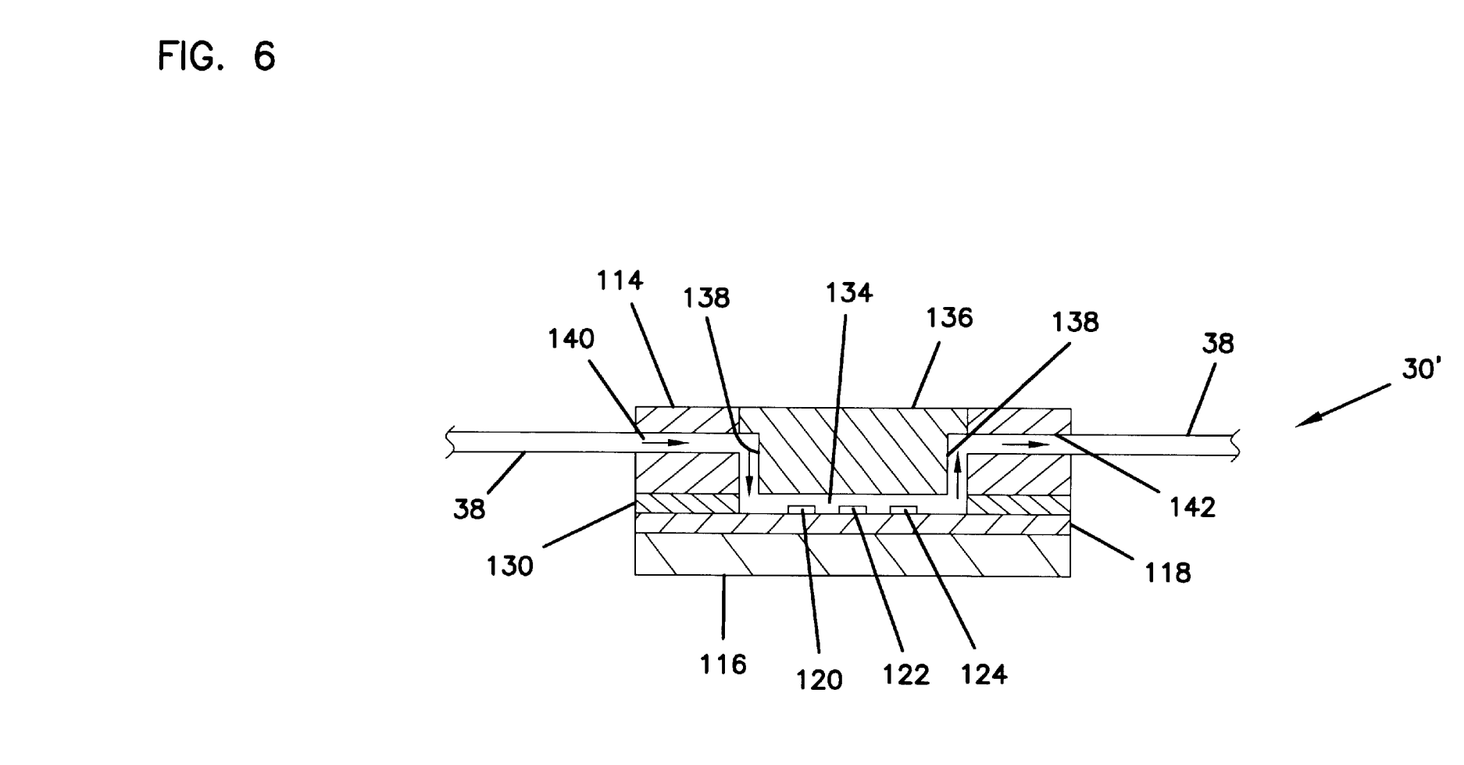
FIG. 6 is a cross-sectional view of the sensor housing of FIG. 5 cut through a flow passage of the housing.

Referring now to FIGS. 5 and 6, a sensor 30' suitable for use with the sensor assembly 20 is shown. The sensor 30' includes a housing 113 having a top piece 114 that is fastened to a bottom piece 116 by conventional techniques such as fasteners (e.g., screws). A substrate 118 is positioned between the top and bottom pieces 114 and 116. The substrate 118 includes a reference electrode 120, a working electrode 122, and a counter electrode 124. The electrodes are coupled to a connector 126 by conductive traces 128. The connector 126 is preferably connected to the controller 144 of the sensor assembly 20. An adhesive layer 130 is positioned between the circuit board 118 and the top piece 114. The adhesive layer 130 defines a slot 132 that extends across the electrodes 120, 122 and 124. In this manner, the slot 132 functions to define a test chamber 134 within the housing 113 of the sensor 30'.

Fluid flowing through the first flow line 38 flows in a direction D through the sensor housing 113. A flow path through the sensor housing is at least partially defined by a resilient (e.g., urethane) member 136 that is press fit within the top piece 114. The resilient member 136 has ends defining notches 138 that each provide a transverse (i.e., upright) flow path within the sensor housing 1 13. For example, as shown in FIG. 6, flow within the first flow line 38 enters the sensor housing through a first port 140, flows downward along one of the notches 138 to the test chamber 134, flows along the test chamber 134 across the electrodes 120, 122 and 124, flows upward along the other notch 138, and exits the sensor housing through a second port 142.

The sensor 30' is preferably a wired enzyme sensor for detecting or measuring bioanalytes. Illustrative wired enzyme sensors are described in U.S. Pat. Nos. 5,264,105; 5,356,786; 5,262,035; and 5,320,725, herein incorporated by reference.

Referring back to FIG. 5, the reference, working and counter electrodes 120, 122 and 124 are formed as separate conductive lines or traces on the substrate 118. At least portions of the reference, working and counter electrodes 120, 122 and 124 are positioned along the test chamber 134 of the sensor 30' when the sensor 30' is assembled as shown in FIG. 6.

The working electrode 122 is the electrode at which an analyte such as lactate or glucose is electrooxidized or electroreduced. Current is passed between the working electrode 122 and the counter electrode 124. The potential of the working electrode 122 is monitored relative to the reference electrode 124. Since essentially no current is passed through the reference electrode 120, its potential will remain constant and equal to its open-circuit value. This system is called a three-electrode system.

If the current is small, a two-electrode system can be used. That is, the counter electrode 124 can be used as a working electrode too, and the reference electrode 120 will also act a counter electrode. Since the current is small, the passage of the low current through the reference electrode 120 will not effect the potential of the reference electrode 120.

The reference, working and counter electrodes 120, 122 and 124 are positioned within the test chamber 134. The chamber 134 is configured so that when a sample is provided in the chamber 134, the sample is in fluid contact with the reference, working, and counter electrodes 120, 122 and 124. This allows electrical current to flow between the electrodes 120, 122 and 124 to effect the electrolysis (electrooxidation or electroreduction) of the analyte.

The working/counter electrodes 122 and 124 may be formed by any conductive material. Exemplary conductive materials include carbon, gold, platinum, graphite, palladium and tin oxide. The working electrodes 122 preferably have test surfaces that are covered with a sensing layer. The sensing layer preferably includes a redox compound or mediator. The term redox compound is used herein to mean a compound that can be oxidized and reduced. Exemplary redox compounds include transition metal complexes with organic ligands. Preferred redox compounds/mediators are osmium transition metal complexes with one or more ligands having a nitrogen containing heterocycle such as 2,2'-bipyridine. The sensing layer can also include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In systems such as the one being described, these enzymes catalyze the electrolysis of an analyte by transferring electrons between the analyte and the electrode via the redox compound.

The reference electrode 120 can be constructed in a manner similar to the working/counter electrodes 122 and 124. Suitable materials for the reference electrode include Ag/AgCl printed on a non-conducting base material or silver chloride on a silver metal base.

In use of the electrochemical sensor 30', a previously determined potential is applied across the reference and working electrodes 120 and 122. When the potential is applied and a sample fluid containing the desired analyte is in the test chamber 134, an electrical current will flow between the working electrode 122, counter electrode 124 and reference electrode 120. The current is a result of the electrolysis of the analyte in the sample fluid. This electrochemical reaction occurs via the redox compound and the optional redox enzyme. By measuring the current flow generated at a given potential, the concentration of a given analyte in a test sample can be determined.

Those skilled in the art will recognize that current measurements can be obtained by a variety of techniques including, among other things, coulometric, potentiometric, amperometric, voltammetric, and other electrochemical techniques.

The measurements obtained by typical non-coulometric techniques are generally temperature dependent. Consequently, temperature data generated by a temperature probe is used to generate reliable analyte data for such techniques. In certain embodiments of the present invention, a temperature probe can be formed as a line on the substrate 118. Alternatively, temperature probes can be located elsewhere within the chamber 134, outside the test chamber 134, or at alternative locations along the flow path 38. The temperature probes preferably interface with the control unit 144.

Referring back to FIG. 1, it is preferred for the catheter 22 of the sensor assembly 20 to be a conventional peripheral catheter. Of course, other types of catheters can also be utilized for withdrawing test fluids from a patient. The first, second and third flow lines 36, 38 and 40 of the sensor assembly 20 are preferably formed by conventional medical tubing.

By way of a non-limiting example, the source of calibration fluid 32 of the sensor assembly 20 can be a conventional intravenous (IV) bag that feeds calibration fluid to the adapter 28 via gravity through the second flow line 38. Of course, other devices, such as syringe pumps, pneumatic pumps and peristaltic pumps, can also be used. A preferred calibration fluid includes a predetermined concentration of a calibrant such as lactate for lactate sensors, or glucose for glucose sensors. The calibration fluid can include a variety of other components in addition to a calibrant. For example, an anticoagulant such as sodium citrate can be used. A preferred calibration fluid comprises a solution of sodium citrate, saline and lactate. Of course, lactate is only used as a calibrant if a lactate sensor is being used in the system. Other types of calibrants that may be used in the system include glucose, potassium, sodium, calcium and ringers lactate.

To start operation of the sensor assembly 20, a patient is prepped and the catheter 22 is inserted at an appropriate site (e.g., the patient's lower arm). The source of calibration fluid 32 and the waste container 36 are then placed at the appropriate locations. For example, if the source of calibration fluid 32 comprises an intravenous (IV) bag, such bag is hung at a level sufficiently above the catheter insertion site to ensure adequate infusion to the patient. Also, if the waste container 36 comprises a conventional waste bag, such bag is preferably hung at a level below the catheter insertion site. Once the various components of the system have been assembled, the system is purged of air and the adapter 28 is mounted to the hub 26 (i.e., the luer fitting) of the catheter 22.

Figure 7:
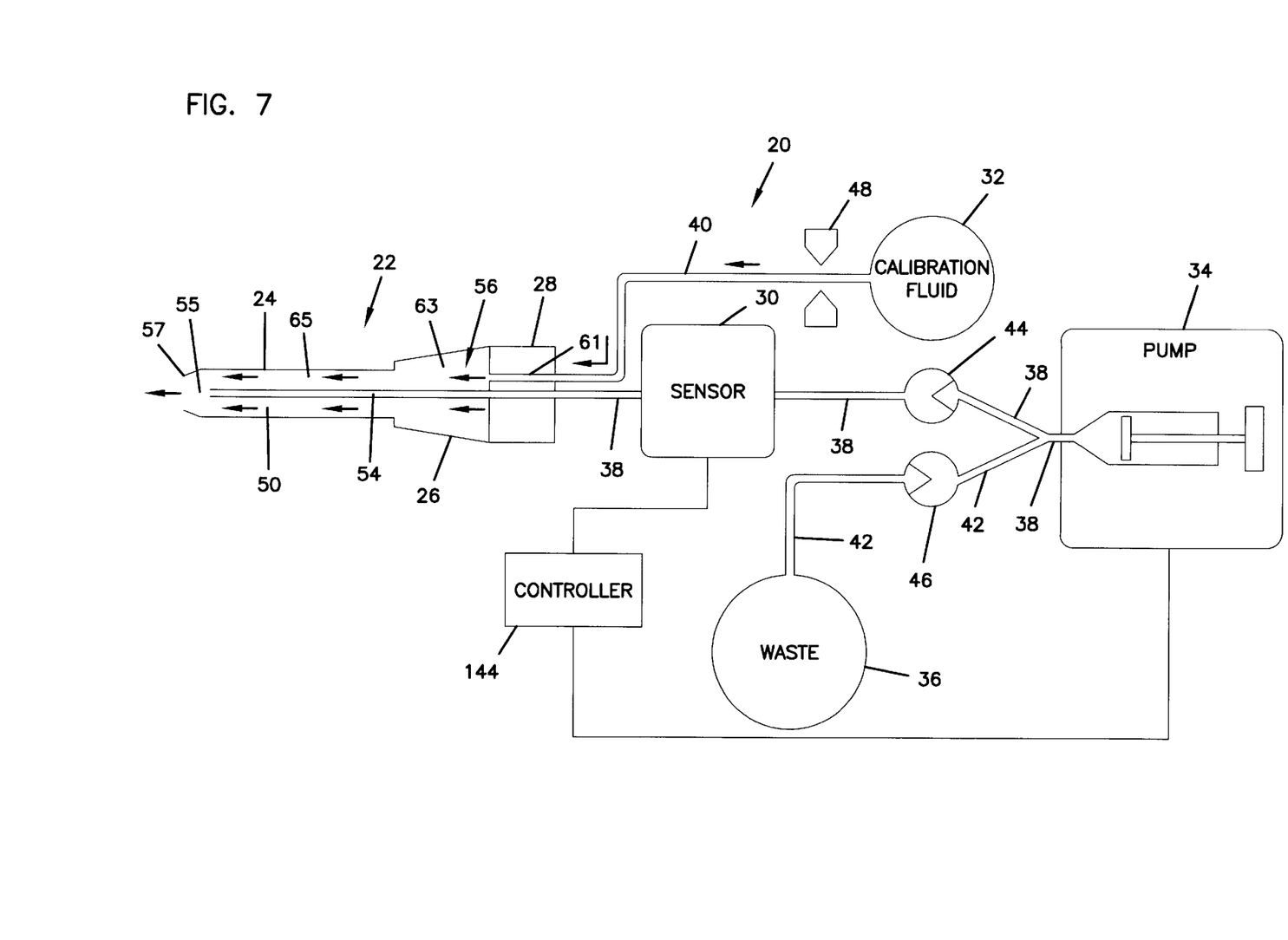
FIG. 7 is a schematic illustration of the sensor assembly of FIG. 1 during a start-up phase.

Once the sensor assembly 20 is assembled as described above, the pinch valve 48 of the second flow line 40 is opened thus beginning an infusion of the calibrant into the patient. For example, as shown in FIG. 7, the calibration fluid flows from the source of calibration fluid 32 to the adapter 28. From the adapter 28, the calibration fluid flows through the second passage 56 into the fluid exchange region 55 defined within the catheter sheath 24. From the fluid exchange region 55, the calibration fluid infuses into the patient.

Figure 8:
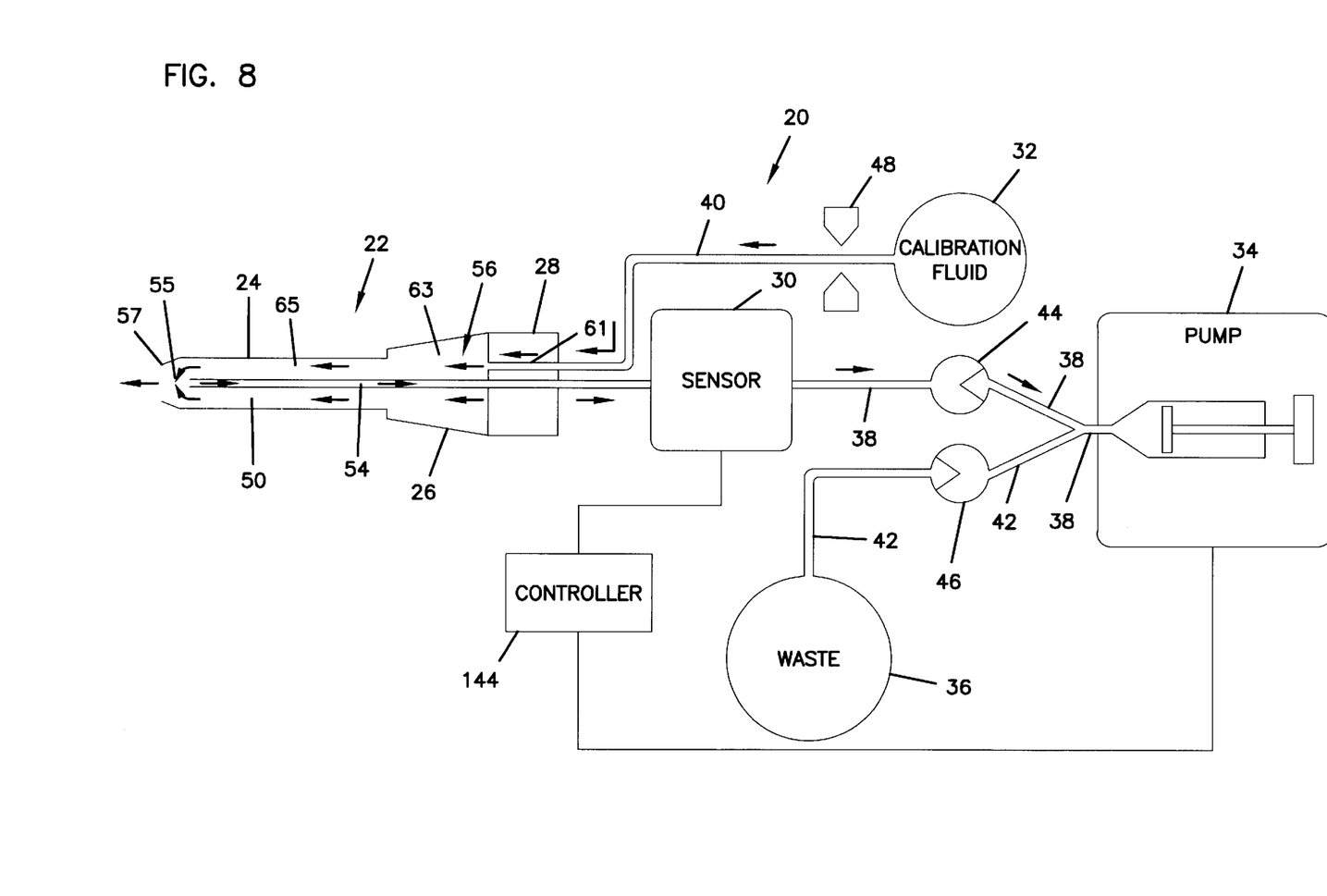
FIG. 8 is a schematic illustration of the sensor assembly of FIG. 1 during a calibration phase.

After flow of calibration fluid has been established to the patient, a calibration phase is initiated in which the pump 34 (e.g., a syringe drawn by a conventional syringe driver) generates a lower pressure gradient that causes the calibration fluid within the fluid exchange region 55 of the catheter sheath 24 to be drawn into the first passage 54 (as shown in FIG. 8). From first passage 54, the calibration fluid flows into the first flow line 38 toward the sensor 30. Preferably, the flow of calibration fluid toward the patient is regulated so as to always be in a ratio of at least two times the draw rate of the pump 34. For example, in one particular embodiment, the flow rate through the first flow line 38 toward the sensor 30 is about 50 microliters per minute, while the flow rate of calibration fluid through the second flow line 40 toward the adapter 28 is about 100 microliters per minute. Consequently, calibration fluid flows into the fluid exchange region 55 from the second passage 56 at twice the flow rate that the calibration fluid is drawn from the fluid exchange region 55 through the first passage 54. As the pump 34 draws fluid toward itself, the first check valve 44 is opened to allow fluid to travel through the first flow line 38 toward the pump 34, while the second check valve 46 is closed to prevent flow from reaching the pump 34.

During the calibration phase, the calibration fluid from the source of calibration fluid 32 flows from the second flow line 40 into the second passage 56. The second passage 56 conveys the calibration fluid to the fluid exchange region 55. When the pump 34 draws upon the first flow line 38, calibration fluid from the third portion 65 of the second passage 56 (i.e., within the sheath concentrically about the first passage 54) is drawn in a concentric path into the open end of the first flow passage 54. Such a concentric configuration, in combination with the two times flow rate provided by the second flow line 40, promotes the pump 34 to draw only the calibration fluid up the conduit 66 and into the first flow line 38. Excess calibration fluid flows out the catheter sheath 24 and into the patient thereby preventing blood from entering the fluid exchange region 55.

Figure 9:
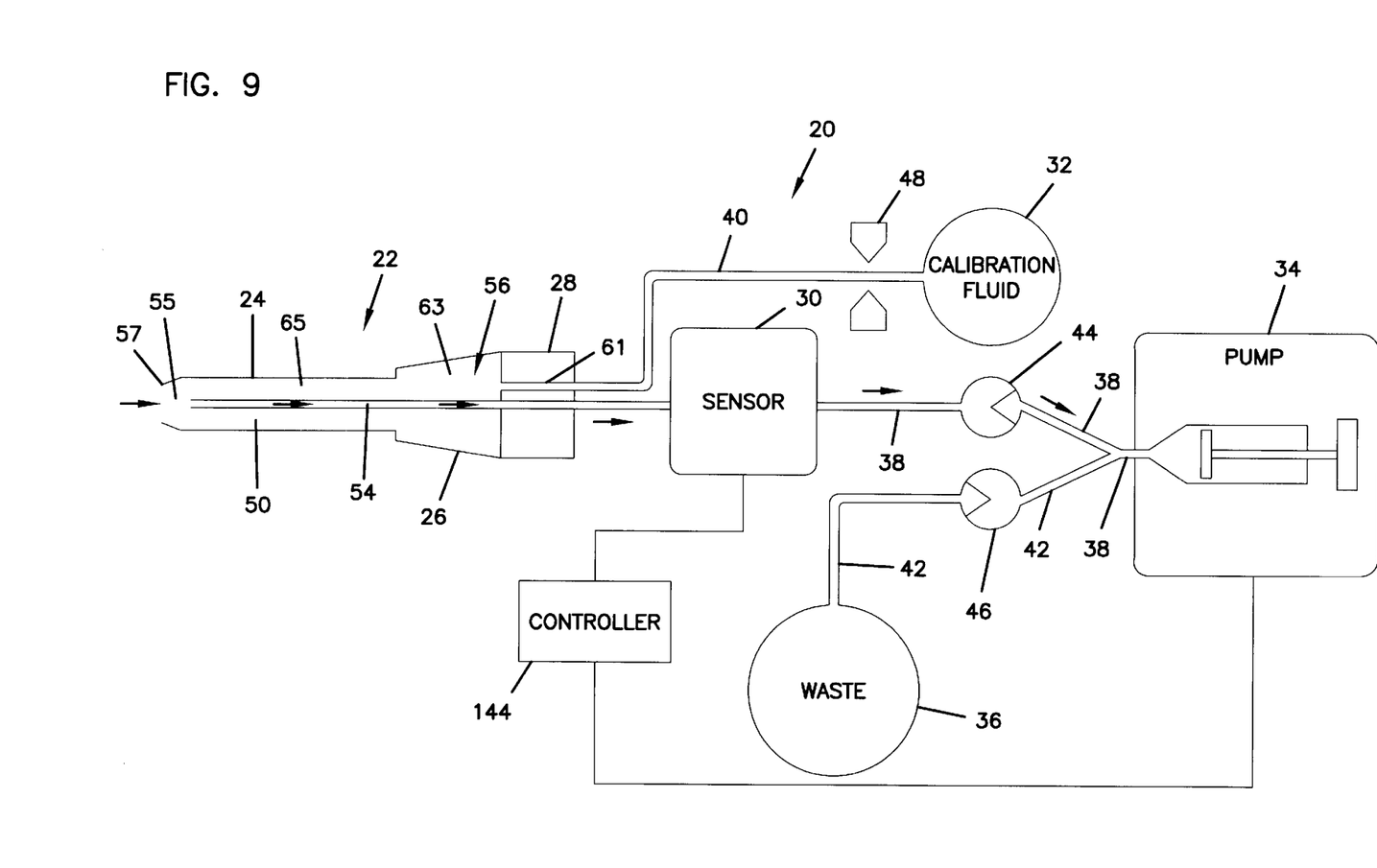
FIG. 9 is a schematic illustration of the sensor assembly of FIG. 1 during a testing phase.

While the flow conditions described above are maintained, the sensor 30 can be calibrated and kept free of blood protein attachment or blockage by clots. When a lactate analysis is desired, the pinch valve 48 is used to close the second flow line 40 (as shown in FIG. 9). By closing the second flow line 40, the flow of calibration fluid to the adapter 28 is stopped. Once the flow of calibration fluid to the adapter 28 is stopped, the pump 34 will soon evacuate the fluid exchange region 55 of its remaining volume of calibration fluid and cause a sample fluid (e.g., blood) to flow from the patient into the catheter sheath 24. From the catheter sheath 24, the blood travels through the first passage 54 into the first flow line 38. The first flow line 38 carries the blood to the sensor 30. After a mixed sample containing a mixture of sample fluid and calibration fluid passes through the sensor 30, a substantially calibrant free volume of sample fluid will be drawn into the sensor 30. When the substantially calibrant free sample fluid has been drawn into the sensor 30, a measurement (e.g., a lactate measurement) can be taken by the sensor 30.

Figure 10:
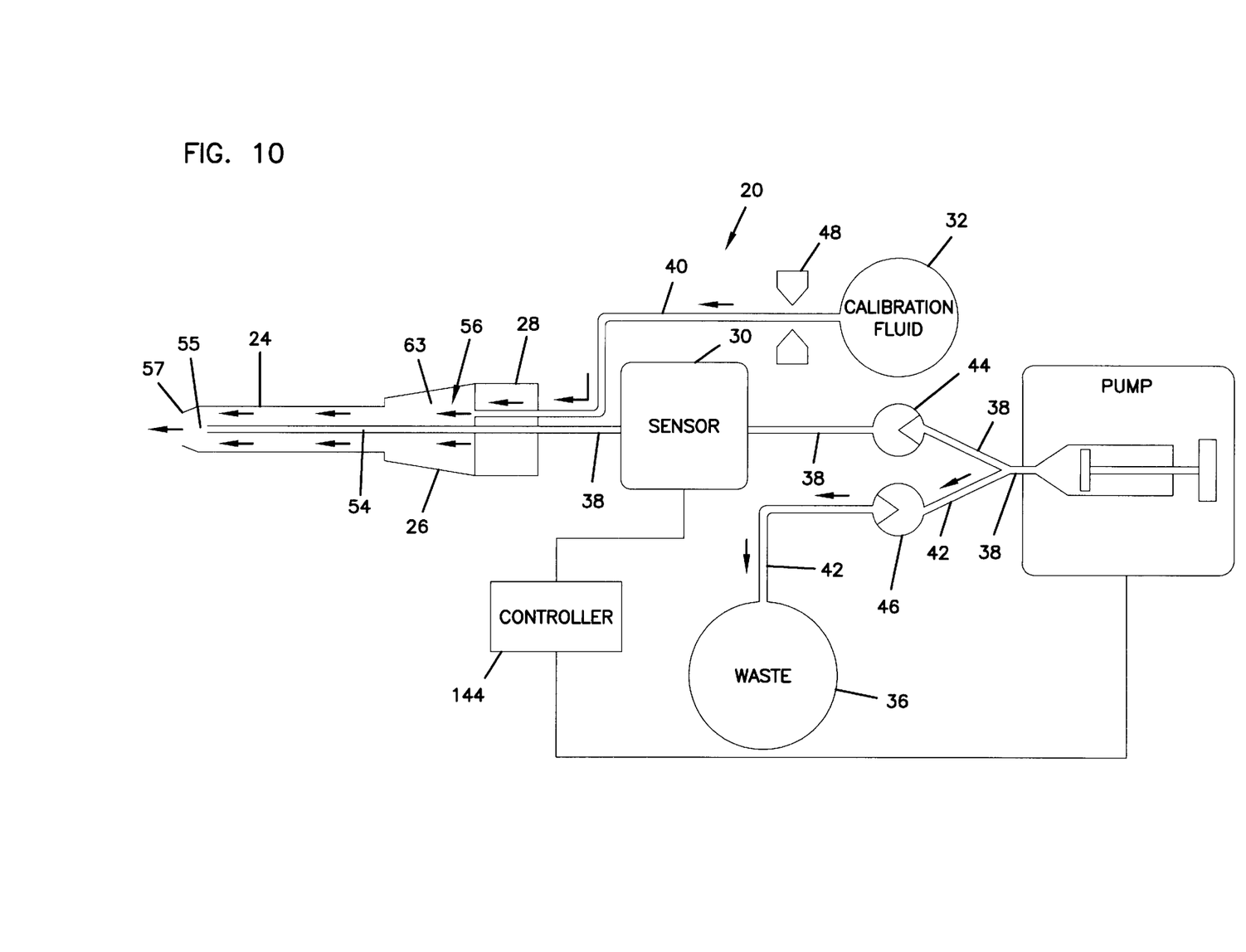
FIG. 10 is a schematic illustration of the sensor assembly of FIG. 1 during a waste discharge phase.

A pump such as a small volume syringe (e.g., about 3 cubic centimeters (cc)) offers the advantage of increased control of flow rates through the first flow line 38. Such a syringe will allow a single draw of approximately 1 hour out of a sensor life cycle of about 10 hours, thus requiring ten purge cycles of the syringe per sensor life. The syringe purge is accomplished by commanding the pump 34 (e.g., a syringe driven by a syringe driver) to reverse direction at a predetermined rate of travel (as shown in FIG. 10). By reversing the pump direction, fluid within the first flow line 38 will be pushed back against the direction of normal flow, thereby causing/allowing the first check valve 44 to close. Concurrently, the reverse flow in the first flow line 38 causes the second check valve 46 located along the third flow line 42 to open. Consequently, flow proceeds through the third flow line 42 and into the waste container 36 (e.g., a waste bag). During this phase, the second flow line 40 is preferably opened to allow calibration fluid to flow through the catheter 22 to inhibit clotting. After the waste discharge phase has been completed, the system can return to the calibration phase of FIG. 8 until a new test sample is desired to be drawn.

Alternatively, a large volume syringe in the range of 30 cc to 60 cc can be used if such use does not induce detrimental flow characteristics to the system. The total volume of the syringe could be equal to the greatest anticipated waste volume for a given sensor life cycle, thus eliminating the need for the check valves 44 and 46 and for the waste container 36.

For certain applications, the control unit 144 can be programmed to cause the sensor arrangement 20 to take fluid samples at predetermined time intervals. For example, samples can be taken every hour, or every fifteen minutes, or every five minutes. During the time periods between sampling, the sensor 30, is preferably bathed in calibration fluid.

The sensor arrangement 20 is particularly suited for use as a disposable ex vivo lactate monitor. When used as a lactate monitor, the sensor arrangement 20 can automatically, via the controller 144, sample lactate readings at predetermined intervals such as every hour, every fifteen minutes, or every five minutes. Current lactate readings can be displayed on a display unit. Furthermore, trends such as increases in lactate concentration, decreases in lactate concentration, and rates of lactate concentration change can be stored in memory associated with the controller 144. Such information can be used to provide a physician with a data such as a lactate history line or an average lactate reading for a particular patient on a given day.

With regard to the foregoing description, it is to be understood that changes may be made in detail, especially in matters of construction materials employed and the shape, size and arrangement of the parts without departing from the scope of the present invention. It is intended that the specification and depicted aspects be considered exemplary only, with a true scope and spirit of the invention being indicated by the broad meaning of the following claims.

What is claimed is:

1. A sensor assembly comprising:
    a catheter including a catheter sheath adapted for insertion in a patient, and a catheter hub connected to the catheter sheath;
    an adapter connected to the catheter hub, the adapter including first and second ports;
    a pump;
    a first flow line extending between the adapter and the pump, the first flow line being connected to the first port of the adapter;
    a sensor positioned along the first flow line;
    a container for holding a calibration fluid, the calibration fluid including a calibrant adapted for use in calibrating the sensor;
    a second flow line extending between the adapter and the container, the second flow line being connected to the second port of the adapter; and
    the adapter defining first and second separate passages, the first passage extending from the first port to an interior region of the catheter sheath, and the second passage extending from the second port to an interior region of the catheter hub.

2. The sensor assembly of claim 1, wherein the sensor comprises a lactate sensor.

3. The sensor assembly of claim 1, wherein the container comprises an intravenous bag.

4. The sensor assembly of claim 1, wherein the pump comprises a syringe.

5. The sensor assembly of claim 1, wherein the adapter includes an insertion portion that fits within the catheter hub, wherein the first passage is defined by a conduit that extends through the insertion portion, and wherein the conduit has an end portion that extends outward from the insertion portion and into the catheter sheath.

6. The sensor assembly of claim 5, wherein the insertion portion includes a frustral conical shaped portion, wherein the frustral conical shaped portion has a first end having a minor diameter and a second end having a major diameter, and wherein the end portion of the conduit projects axially outward from the first end.

7. The sensor assembly of claim 5, wherein the insertion portion of the adapter defines at least a portion of the second passage.

8. The sensor assembly of claim 7, wherein the portion of the second passage defined by the insertion portion of the adapter at least partially surrounds the conduit defining the first passage.

9. The sensor assembly of claim 7, wherein the portion of the second passage defined by the insertion portion of the adapter concentrically surrounds the conduit defining the first passage.

10. The sensor assembly of claim 1, wherein first passage is at least partially defined by a conduit that extends into the catheter sheath and terminates adjacent a distal tip of the catheter sheath.

11. The sensor assembly of claim 10, wherein the conduit terminates at a location not greater than 1 centimeter from the distal tip of the catheter sheath.

12. The sensor assembly of claim 10, wherein the conduit terminates at a location not greater than 1 millimeter from the distal tip of the catheter sheath.

13. A sensor assembly comprising:
    a catheter including a catheter sheath adapted for insertion in a patient;
    first structure defining a first flow passage that extends within the catheter sheath and terminates within an interior region of the catheter sheath;
    second structure defining a second flow passage separate from the first flow passage, the second flow passage terminating within the interior region of the catheter sheath;
    a sensor positioned in fluid communication with the first flow passage;
    a source of calibration fluid in fluid communication with the second flow passage, the source of calibration fluid including calibration fluid that is conveyed to the interior region of the catheter sheath through the second flow passage, the calibration fluid being adapted for use in calibrating the sensor; and a pump in fluid communication with the first flow passage, the pump being adapted for drawing a fluid from the interior region of the catheter sheath to the sensor.

14. The sensor assembly of claim 13, wherein the first structure includes a conduit inserted within the catheter sheath, the conduit at least partially defining the first flow passage, and the conduit having an end positioned within the catheter sheath at a location adjacent a distal tip of the catheter.

15. The catheter assembly of claim 14, wherein the second flow passage is at least partially defined between the conduit and the catheter sheath.

16. The catheter assembly of claim 14, wherein at least a portion of the second passage circumferentially surrounds the conduit within the catheter sheath.

17. An adapter for use with a catheter including a catheter sheath connected to a catheter hub, the catheter sheath being adapted for insertion in a patient, the adapter comprising:

an adapter body defining first and second ports adapted for connection to medical tubing;

a connecting member adapted to fasten the adapter body to the hub;

a conduit extending from the first port through the adapter body, the conduit including an end portion that projects outward from the adapter body, the end portion being arranged and configured to fit within an interior region of the catheter sheath when the adapter body is connected to the catheter hub; and structure defining a passage separate from the conduit that extends from the second port through the adapter body, the passage being arranged and configured to provide fluid communication between the second port and an interior region of the catheter hub when the adapter body is connected to the catheter hub.

18. The sensor assembly of claim 17, wherein the adapter includes an insertion portion sized and shaped to fit within the catheter hub, and wherein the end portion of the conduit extends outward from the insertion portion.

19. The sensor assembly of claim 18, wherein the insertion portion includes a generally frustral conical shaped portion, wherein the frustral conical shaped portion has a first end having a minor diameter and a second end having a major diameter, and wherein the end portion of the conduit projects axially outward from the first end.

20. The sensor assembly of claim 18, wherein the insertion portion of the adapter defines at least a portion of the passage.

21. The sensor assembly of claim 20, wherein the portion of the second passage defined by the insertion portion of the adapter at least partially surrounds the conduit within the insertion portion.

22. The sensor assembly of claim 20, wherein the portion of the second passage defined by the insertion portion of the adapter concentrically surrounds the conduit within the insertion portion.

23. A method of operating a sensor assembly, the sensor assembly comprising: a catheter including a catheter sheath adapted for insertion in a patient; a conduit defining a first flow passage in fluid communication with a pump, the conduit being inserted within the catheter sheath and including an end positioned adjacent a distal end of the catheter sheath; and a second flow passage defined at least partially between the conduit and the catheter sheath, the method comprising:

inserting the catheter sheath into the patient;

conveying calibration fluid through the second flow passage to a fluid exchange region located within the catheter sheath adjacent the distal tip of the catheter sheath;

calibrating the sensor by drawing the calibration fluid from the fluid exchange region through the first flow passage, and conveying the calibration fluid past the sensor;

terminating the conveyance of calibration fluid to the fluid exchange region;

drawing a test sample from the patient into the fluid exchange region after the conveyance of calibration fluid to the fluid exchange region has been terminated;

drawing the test sample from the fluid exchange region through the first flow passage and to the sensor; and sensing the sample fluid with the sensor.

24. The method of claim 23, wherein the sensor comprises a lactate sensor.

25. The method of claim 23, wherein during calibration, the calibration fluid is conveyed to the fluid exchange region of the catheter sheath at a first flow rate that is at least two times as fast as a second flow rate that the calibration fluid is withdrawn from the fluid exchange region and conveyed to the sensor.

* * * * *

UNITED STATES PATENT AND TRADEMARK OFFICE
CERTIFICATE OF CORRECTION

PATENT NO. : 6,128,519    Page 1 of 1
DATED : October 3, 2000
INVENTOR(S) : Say

It is certified that error appears in the above-identified patent and that said Letters Patent is hereby corrected as shown below:

<u>Title page,</u>
Inventor [75]: "James I Say" should read -- James L. Say --

<u>Column 7,</u>
Line 63, "1 13" should read -- 113 --

Signed and Sealed this

Fourteenth Day of May, 2002

*Attest:*

JAMES E. ROGAN
*Attesting Officer*    *Director of the United States Patent and Trademark Office*